US012233226B2

(12) United States Patent
Gessler, III et al.

(10) Patent No.: US 12,233,226 B2
(45) Date of Patent: Feb. 25, 2025

(54) DEVICES AND METHODS FOR TREATING A STRICTURE ALONG THE BILIARY AND/OR PANCREATIC TRACT

(71) Applicant: BOSTON SCIENTIFIC SCIMED, INC., Maple Grove, MN (US)

(72) Inventors: Raymond D. Gessler, III, Roberts, WI (US); Peter L. Dayton, Brookline, MA (US); David B. Joda, St. Paul, MN (US); Kyle L. Lemke, Hudson, WI (US); Jason Matteson, Beldenville, WI (US); Mark P. Olson, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 168 days.

(21) Appl. No.: 17/393,999

(22) Filed: Aug. 4, 2021

(65) Prior Publication Data

US 2022/0040457 A1    Feb. 10, 2022

Related U.S. Application Data

(60) Provisional application No. 63/061,522, filed on Aug. 5, 2020.

(51) Int. Cl.
   *A61M 25/09*    (2006.01)
(52) U.S. Cl.
   CPC ............... *A61M 25/09041* (2013.01); *A61M 2025/09091* (2013.01); *A61M 2025/09116* (2013.01);
   (Continued)
(58) Field of Classification Search
   CPC .. A61M 25/09041; A61M 2025/09091; A61M 2025/09116; A61M 2025/0915;
   (Continued)

(56) References Cited

U.S. PATENT DOCUMENTS 4,886,067 A * 12/1989 Palermo .......... A61M 25/09033
                                                   604/528
5,542,434 A *  8/1996 Imran ................... A61M 25/09
                                                   600/585
(Continued)

FOREIGN PATENT DOCUMENTS

| EP | 812600 A2 | 12/1997 |
| EP | 2636381 A1 | 9/2013 |
| JP | H0788189 A | 4/1995 |

OTHER PUBLICATIONS

International Search Report and Written Opinion dated Dec. 23, 2021 for International Application No. PCT/US2021/044513.

*Primary Examiner* — Devin B Henson
(74) *Attorney, Agent, or Firm* — Seager, Tufte & Wickhem, LLP (57) ABSTRACT

Medical devices and systems for treating a stricture along the biliary and/or pancreatic tract are disclosed. An example medical device may include a guidewire for use along the biliary and/or pancreatic tract. The guidewire may include an elongate core member having a proximal end region and a distal end region. A coil member may be disposed along the distal end region. An actuation member may be coupled to the coil member. The actuation member may be configured to shift the coil member between a first configuration and a compressed configuration. The coil member may be configured to be advanced across a biliary and/or pancreatic stricture when in the compressed configuration. A sleeve may be disposed over the coil member.

20 Claims, 8 Drawing Sheets

(52) U.S. Cl.
CPC .............. *A61M 2025/0915* (2013.01); *A61M 2025/09175* (2013.01); *A61M 2210/1042* (2013.01)

(58) Field of Classification Search
CPC   A61M 2025/09175; A61M 2210/1042; A61B 2017/22038; A61B 2017/22094
See application file for complete search history.

(56) References Cited

U.S. PATENT DOCUMENTS

| | | | |
|---|---|---|---|
| 5,605,162 | A | 2/1997 | Mirzaee et al. |
| 6,183,420 | B1 | 2/2001 | Douk et al. |
| 7,867,176 | B2 * | 1/2011 | Wu ................... A61M 25/09 |
| | | | 600/585 |
| 2009/0198153 | A1 | 8/2009 | Shriver |
| 2009/0254001 | A1 * | 10/2009 | Wright ............... A61M 25/09 |
| | | | 600/585 |
| 2010/0177185 | A1 * | 7/2010 | Woerlein ............ A61B 90/36 |
| | | | 382/128 |
| 2010/0191150 | A1 | 7/2010 | Palme, Jr. et al. |
| 2014/0121642 | A1 * | 5/2014 | Jordan ............... A61M 25/09 |
| | | | 604/528 |
| 2019/0255295 | A1 * | 8/2019 | Spindler ............. A61M 25/09 |
| 2019/0321157 | A1 | 10/2019 | Callaghan et al. |

\* cited by examiner

DEVICES AND METHODS FOR TREATING A STRICTURE ALONG THE BILIARY AND/OR PANCREATIC TRACT

CROSS REFERENCE TO RELATED APPLICATIONS

This application claims the benefit of and priority to U.S. Provisional Patent Application Ser. No. 63/061,522 filed on Aug. 5, 2020, the disclosure of which is incorporated herein by reference.

TECHNICAL FIELD

The present disclosure pertains to medical devices, and methods for manufacturing medical devices. More particularly, the present disclosure pertains to medical devices for treating strictures along the biliary and/or pancreatic tract.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. A guidewire for use along the biliary and/or pancreatic tract is disclosed. The guidewire comprises: an elongate core member having a proximal end region and a distal end region; a coil member disposed along the distal end region; an actuation member coupled to the coil member, the actuation member being configured to shift the coil member between a first configuration and a compressed configuration; wherein the coil member is configured to be advanced across a biliary and/or pancreatic stricture when in the compressed configuration; and a sleeve disposed over the coil member.

Alternatively or additionally to any of the embodiments above, the actuation member includes a wire.

Alternatively or additionally to any of the embodiments above, the actuation member includes a stranded cable.

Alternatively or additionally to any of the embodiments above, the actuation member is secured to a distal end of the coil member.

Alternatively or additionally to any of the embodiments above, further comprising a handle coupled to the actuation member.

Alternatively or additionally to any of the embodiments above, further comprising a tip member disposed adjacent to a distal end of the coil member.

Alternatively or additionally to any of the embodiments above, the sleeve has a constant outer diameter.

A method for antegrade stricture crossing along the biliary and/or pancreatic tract, the method comprising: advancing a variable stiffness guidewire to a position adjacent to a stricture along the biliary and/or pancreatic tract; wherein the variable stiffness guidewire comprises: an elongate core member having a proximal end region and a distal end region, a coil member disposed along the distal end region, an actuation member coupled to the coil member, the actuation member being configured to shift the coil member between a first configuration and a compressed configuration, and a sleeve disposed over the coil member; actuating the actuation member to shift the coil member to the compressed configuration; and advancing the variable stiffness guidewire across the stricture.

Alternatively or additionally to any of the embodiments above, advancing a variable stiffness guidewire to a position adjacent to a stricture along the biliary and/or pancreatic tract includes advancing the variable stiffness guidewire through an endoscope.

Alternatively or additionally to any of the embodiments above, advancing a variable stiffness guidewire to a position adjacent to a stricture along the biliary and/or pancreatic tract includes advancing the variable stiffness guidewire through a wall of the duodenum.

Alternatively or additionally to any of the embodiments above, the actuation member includes a wire.

Alternatively or additionally to any of the embodiments above, the actuation member includes a stranded cable.

Alternatively or additionally to any of the embodiments above, the actuation member is secured to a distal end of the coil member.

Alternatively or additionally to any of the embodiments above, further comprising a handle coupled to the actuation member, and wherein actuating the actuation member includes actuating the handle.

Alternatively or additionally to any of the embodiments above, further comprising a tip member disposed adjacent to a distal end of the coil member.

Alternatively or additionally to any of the embodiments above, the sleeve has a constant outer diameter.

A variable stiffness guidewire is disclosed. The variable stiffness guidewire comprises: an elongate shaft having a proximal end region and a distal end region; a coil member coupled to the distal end region, the coil member having a distal end; an actuation member coupled to the distal end of the coil member and extending toward the proximal end region of the elongate shaft, the actuation member being configured to shift the coil member between a first configuration and a compressed configuration; wherein the coil member is configured to be advanced across a biliary and/or pancreatic stricture when in the compressed configuration; and a sleeve disposed over the coil member.

Alternatively or additionally to any of the embodiments above, further comprising a handle coupled to the actuation member and to the proximal end region of the elongate shaft.

Alternatively or additionally to any of the embodiments above, further comprising a tip member disposed adjacent to the distal end of the coil member.

Alternatively or additionally to any of the embodiments above, the sleeve has a constant outer diameter.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

In endoscopy, a frequent medical condition arises when a patient presents with abdominal pain with or without associated jaundice. The etiology is usually some type of obstruction in the biliary tree which prevents bile from flowing naturally from the proximal tree into the duodenum. The blockage may be the result of biliary stones caught in the lumen of the ducts or a tumor which is either in the wall of the duct or impinging upon the wall from adjacent tissue. When such a stricture occurs the duct proximal to the stricture dilates and the duct distal to the stricture receives a reduced flow of bile. In order to relieve the patient's symptoms, gastroenterologists seek to find a method for resuming the flow of bile from the proximal dilated duct into the duodenum. Some interventions contemplated for relieving symptoms may include placing a stent across the stricture to drain the proximal duct, removing a stone, and/or the like.

The most common method of placing a stent across the stricture is to perform an endoscopic retrograde cholangiopancreatography (ERCP) where a side-viewing endoscope is placed in the duodenum at the location of the biliary papilla and a guidewire is placed through the papilla and up the biliary duct, across the stricture, in a retrograde fashion. Such procedures may be challenging. For example, depending on the location, geometry, and mechanics of the stricture, deep cannulation of the proximal duct may be difficult if not be possible. Furthermore, when the physician attempts to access the biliary duct, they may inadvertently cannulate the pancreatic duct. Inadvertent cannulation of the pancreatic duct could lead to complications such as pancreatitis. Disclosed herein are devices and methods that address these and other issues, for example by utilizing antegrade (e.g., non-papillary) stricture crossing.

Figure 1:
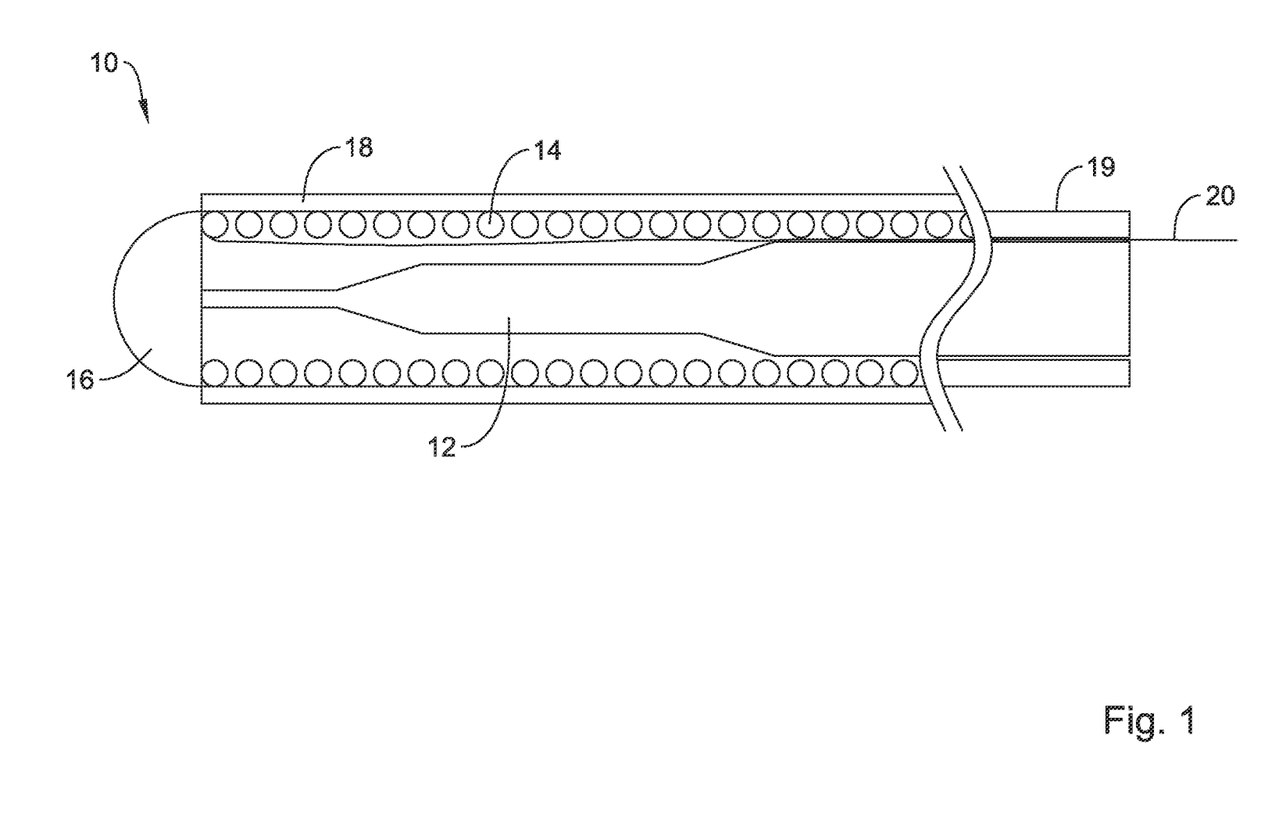
FIG. 1 is a partial cross-sectional side view of a portion of a medical device system according to the present disclosure.

FIG. 1 schematically depicts an example medical device 10 for crossing strictures along the biliary and/or pancreatic tract in accordance with the present disclosure. The medical device 10 may take the form of a guidewire 10 (e.g., a variable stiffness guidewire 10). In general, the guidewire 10 may have a variable stiffness that allows the guidewire 10 to be used for antegrade stricture crossing. This may include the ability to change (e.g., increase) the stiffness of the guidewire 10 during navigation in order to more efficiently cross the stricture.

The structure and form of the guidewire 10 may vary. For example, the guidewire 10 may include a polymer tip, spring tip, angled tip, and/or other structures/configurations. In some instances, the guidewire 10 may include a core member or wire 12. A coil member 14 may be disposed along at least a portion of the core wire 12. In general, the coil member 14 may be configured to shift between a first or uncompressed configuration and a second or compressed configuration. When the coil member 14 is in the first configuration, the guidewire 10 may have a relatively high level of flexibility. When the coil member 14 is shifted to the second configuration, the guidewire 10 may have a relatively high level of stiffness. In at least some instances, the coil member is configured to be advanced across a biliary and/or pancreatic stricture when in the compressed configuration. A tip member 16 may be disposed at a distal end of the coil member 14. In this example, the tip member 16 is depicted as a solder ball tip. However, in other instances, the tip member 16 may take the form of a "floppy" tip, a spring tip, a polymer tip, an angled tip, a tapered tip, and/or the like.

In some instances, the coil member 14 may be replaced by a tubular member having a plurality of slots (e.g., laser cut slots) formed therein. The tubular member may have one or more preferred bending direction, for example determined by the configuration of the slots. In some instances, the tubular member may include one or more steering wires that allow the guidewire 10 to be steered.

A sleeve 18 may be disposed along the coil member 14. The sleeve 18 may have a substantially constant outer diameter. In at least some instances, the sleeve 18 may be configured to keep substantially the same outer diameter regardless of whether the coil member 14 is in the first configuration or the second configuration (and/or any other configuration). The sleeve 18 may include a polymeric material. In at least some instances, the sleeve 18 may include a lubricious material (e.g., the sleeve 18 may be formed from a lubricious material and/or the sleeve 18 may include a lubricous layer or coating). In some instances, the sleeve 18 may have insulating properties, which may allow the guidewire 10 to be used with radiofrequency or other electrical devices. The sleeve 18 may also provide the coil member 14 with a level of torsional support/strength (e.g., when the coil member 14 is in the first configuration) that allows a clinician to efficiently apply torque to the guidewire 10 or otherwise steer the guidewire 10 toward a target (e.g., a stricture along the biliary and/or pancreatic tract). In some instances, the guidewire 10 may be free of the sleeve 18 (e.g., a sleeve like the sleeve 18 is not positioned along the coil member 14).

In some instances, the coil member 14 is disposed along a distal portion of the guidewire 10. In at least some of these instances, a shaft or tubular member 19 may extend proximally from a proximal end of the coil member 14. The tubular member 19 may take the form of a hyoptube. In other instances, the coil member 14 may extend along some or all of the proximal portion of the guidewire 10. For example, in some instances the coil member 14 may extend to the proximal end of the guidewire 10.

Figure 2:
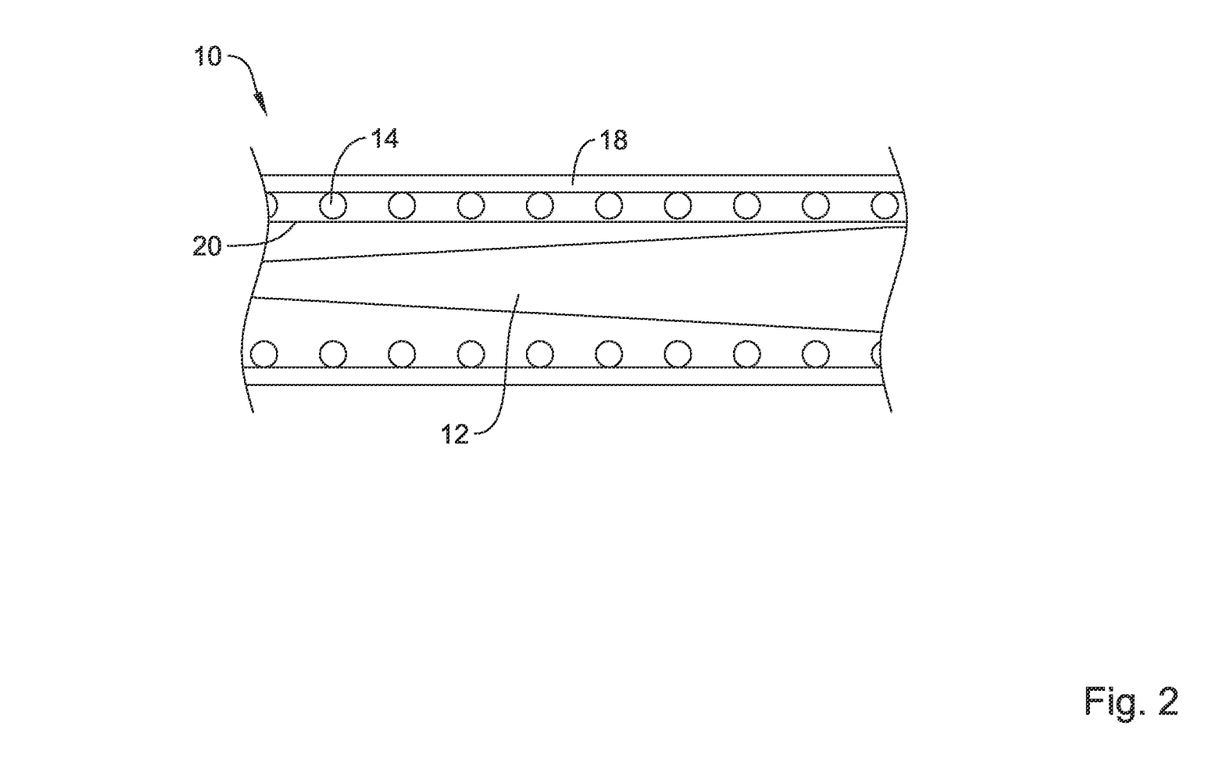
FIG. 2 is a partial cross-sectional side view of a portion of a medical device system according to the present disclosure.
Figure 3:
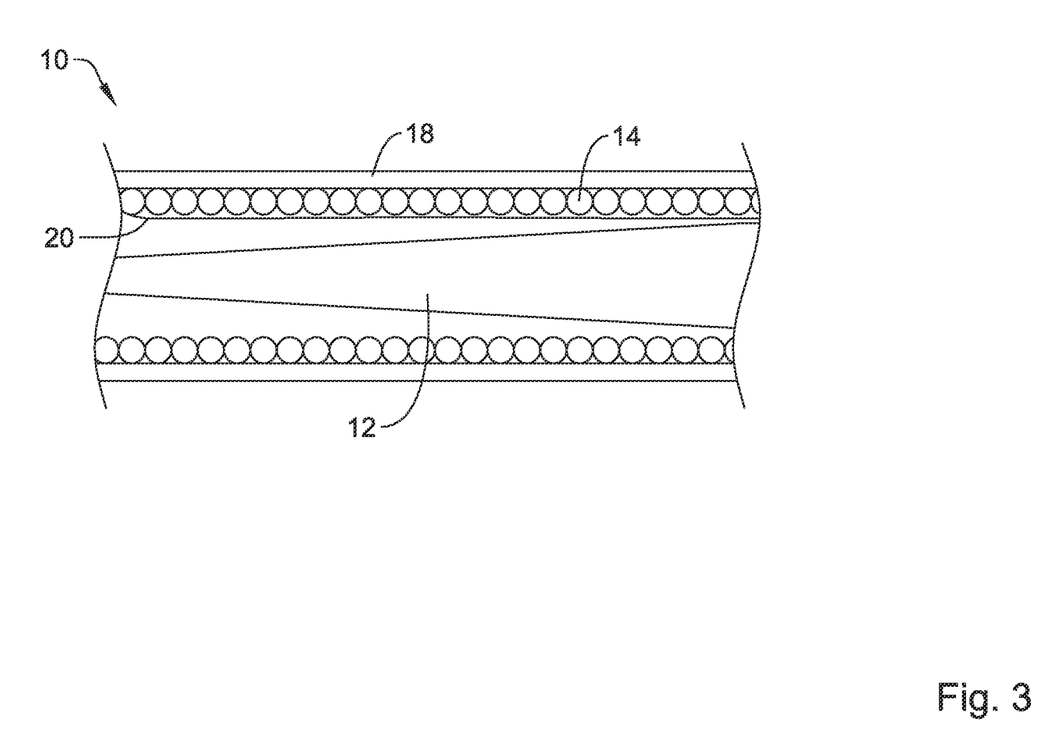
FIG. 3 is a partial cross-sectional side view of a portion of a medical device system according to the present disclosure.

An actuation member 20 may be coupled to the coil member 14. The actuation member 20 may take of the form of a wire (e.g., a round wire, a ribbon wire, a stranded wire, a stiffened rod, and/or the like) that extends along the interior or the exterior of the coil member 14 toward the proximal end of the guidewire 10. In at least some instances, the actuation member 20 may be attached to the distal end of the coil member 14. The actuation member 20 may be configured to shift the coil member 14 between a first or uncompressed configuration (e.g., as shown in FIG. 2) and a second or compressed configuration (e.g., as shown in FIG. 3). For example, the actuation member 20 may be proximally retracted (e.g., pulled/tensioned) to apply compressive forces onto the coil member 14. It can be appreciated that as the actuation member 20 is further tensioned, additional compressive force is applied to the coil member 14, which increases the stiffness of the guidewire 10. While the configurations of the coil member 14 may be considered to be described as binary in nature (e.g., a first and a second configuration), in reality the state of the coil member 14 may be understood as being shifted across a range of configurations that result in a continuum of flexibility/stiffness characteristics for the guidewire 10.

Figure 4:
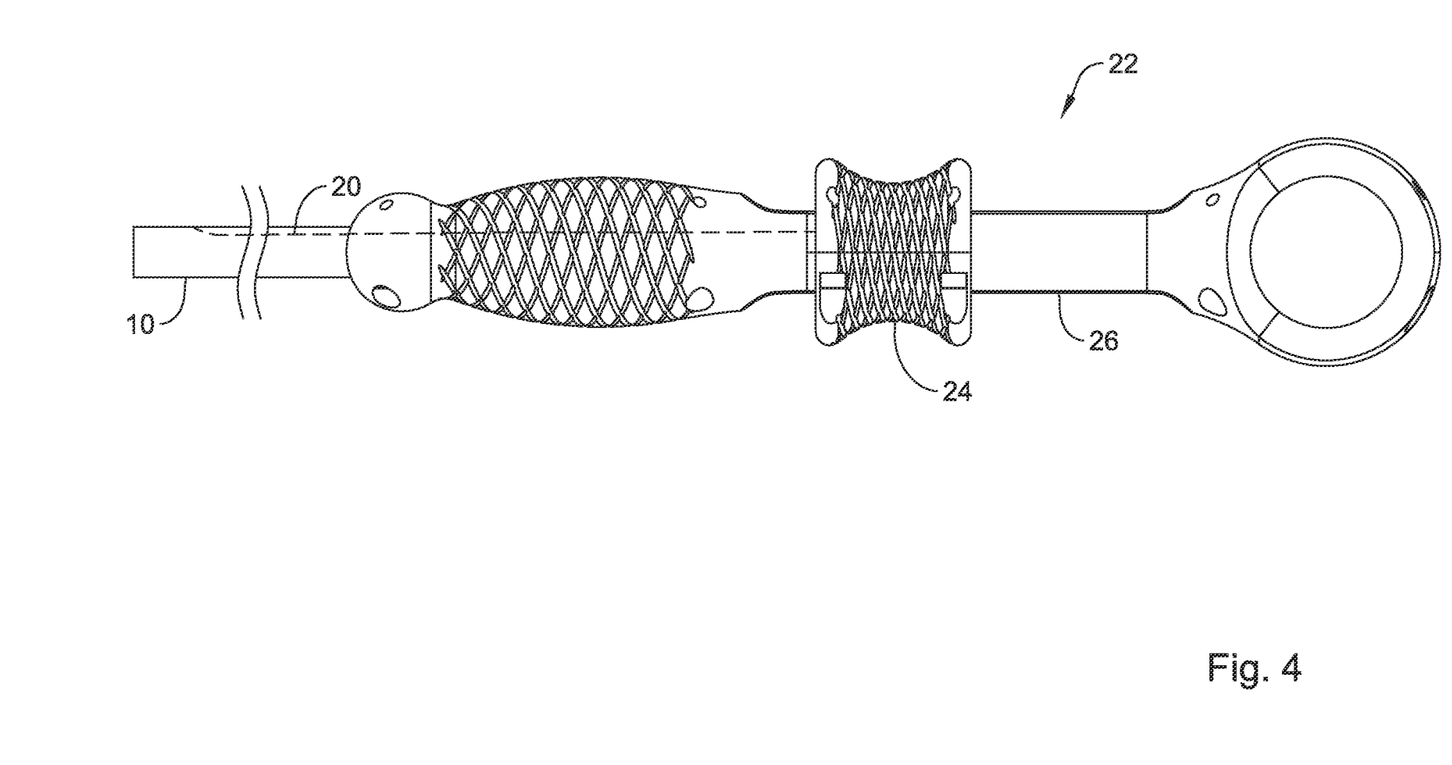
FIG. 4 is a partial cross-sectional side view of a portion of a medical device system according to the present disclosure.

FIG. 4 illustrates a handle 22 may be coupled to the guidewire 10. The handle 22 may include a slidable member 24 that can slide along a region 26 of the handle 22. The slidable member 24 may be coupled to the actuation member 20. Thus, proximal movement of the slidable member 24 may result in proximal retraction of the actuation member 20 (e.g., and increased stiffness of the guidewire 10). In some instances, the handle 22 may include a lock configured to secure the axial position of the slidable member 24 relative to the region 26.

Figure 5:
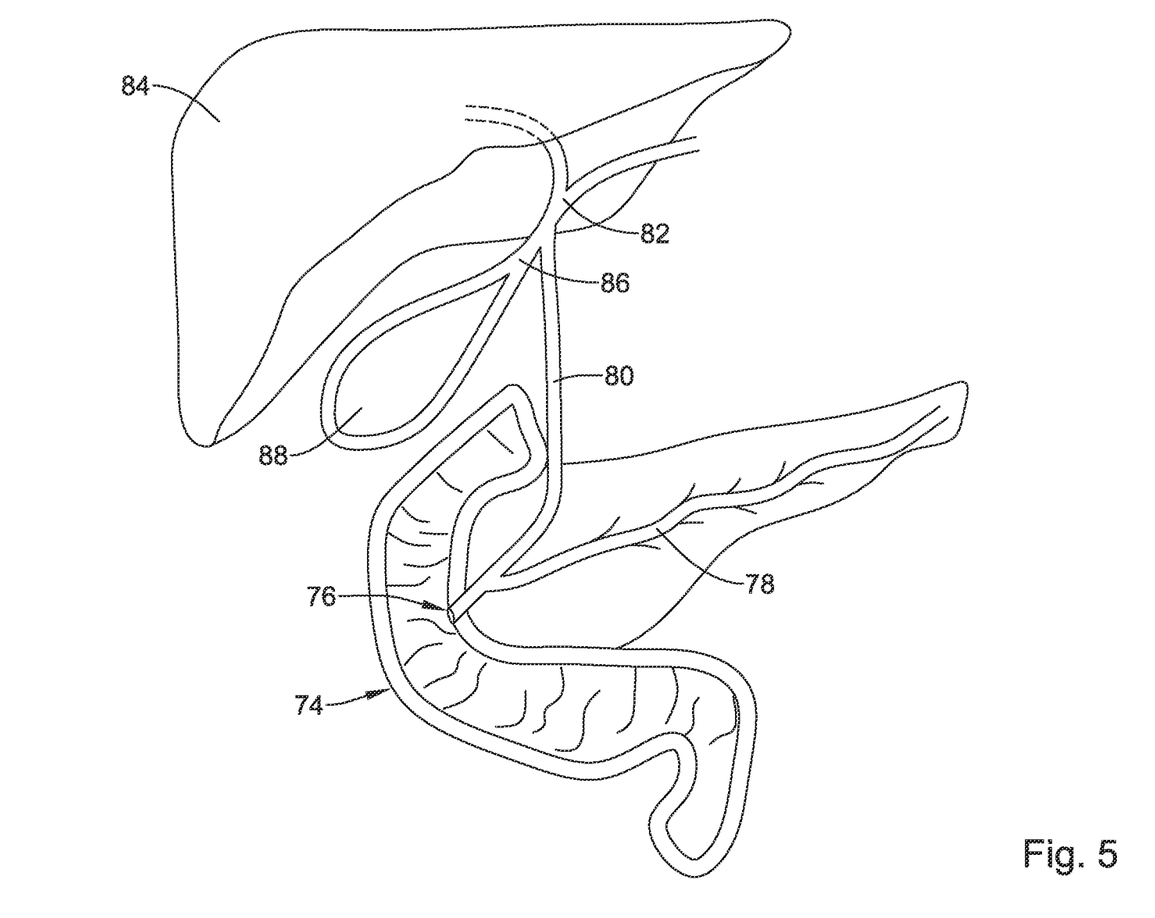
FIG. 5 is a partial cross-sectional side view of a portion of a medical device system according to the present disclosure.

FIG. 5 illustrates an overview of the biliary system or tree. A portion of the duodenum 74 is shown. The papilla of Vater 76 (e.g., also known as the ampulla of Vater or simply the papilla) is located at the illustrated portion of the duodenum 74. The papilla 76 generally forms the opening where the pancreatic duct 78 and the common bile duct 80 can empty into the duodenum 74. The hepatic ducts, denoted by the reference numeral 82, are connected to the liver 84 and empty into the bile duct 80. Similarly, the cystic duct 86, being connected to the gall bladder 88, also empties into the bile duct 80. In general, an endoscopic or biliary procedure may include advancing a medical device to a suitable location along the biliary tree and then performing the appropriate intervention.

Figure 6:
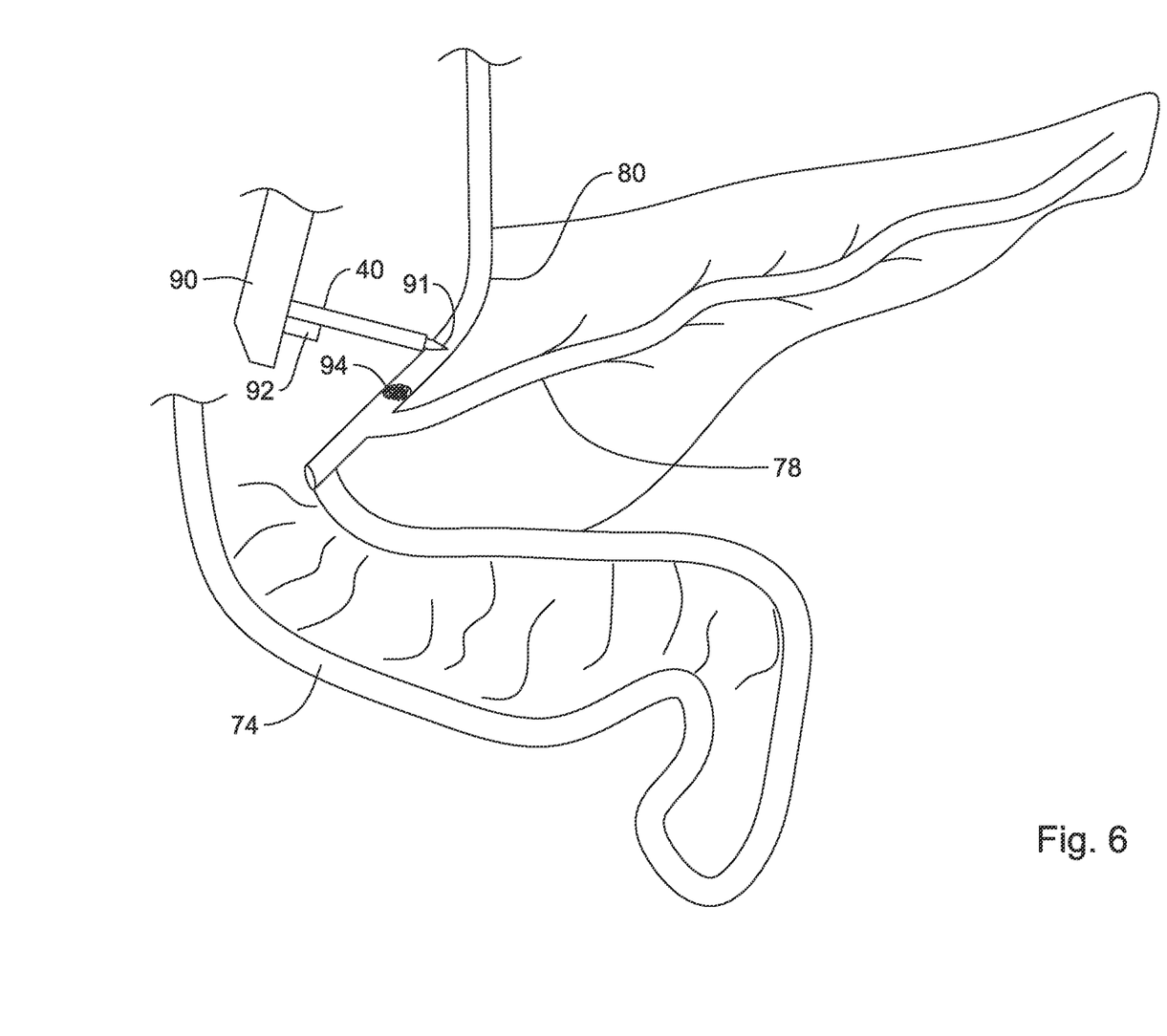
FIGS. 6-8 illustrate a method for using a medical device system according to the present disclosure.

In some instances, it may be desirable to navigate the guidewire 10 past a stricture 94 along the pancreatic and/or biliary tract. This may include an antegrade crossing procedure (as opposed to a retrograde or papillary crossing procedure). For example, FIG. 6 depicts an endoscope 90 extending into the duodenum 74. In some instances, a catheter or introducer sheath 40 may be advanced through the endoscope 90 (e.g., through a channel formed in the endoscope 90). The introducer sheath 40 may be directed toward the wall of the duodenum 74 with the elevator 92 of the endoscope 90. In some instances, a needle/sharp 91 may be disposed within the introducer sheath 40. The needle/sharp 91 may help to pierce through the wall of the duodenum 74, through tissue, and into a position along the pancreatic and/or biliary tract adjacent to (e.g., proximal to) a stricture 94. In this example, the stricture 94 is disposed along the bile duct 80.

Figure 7:
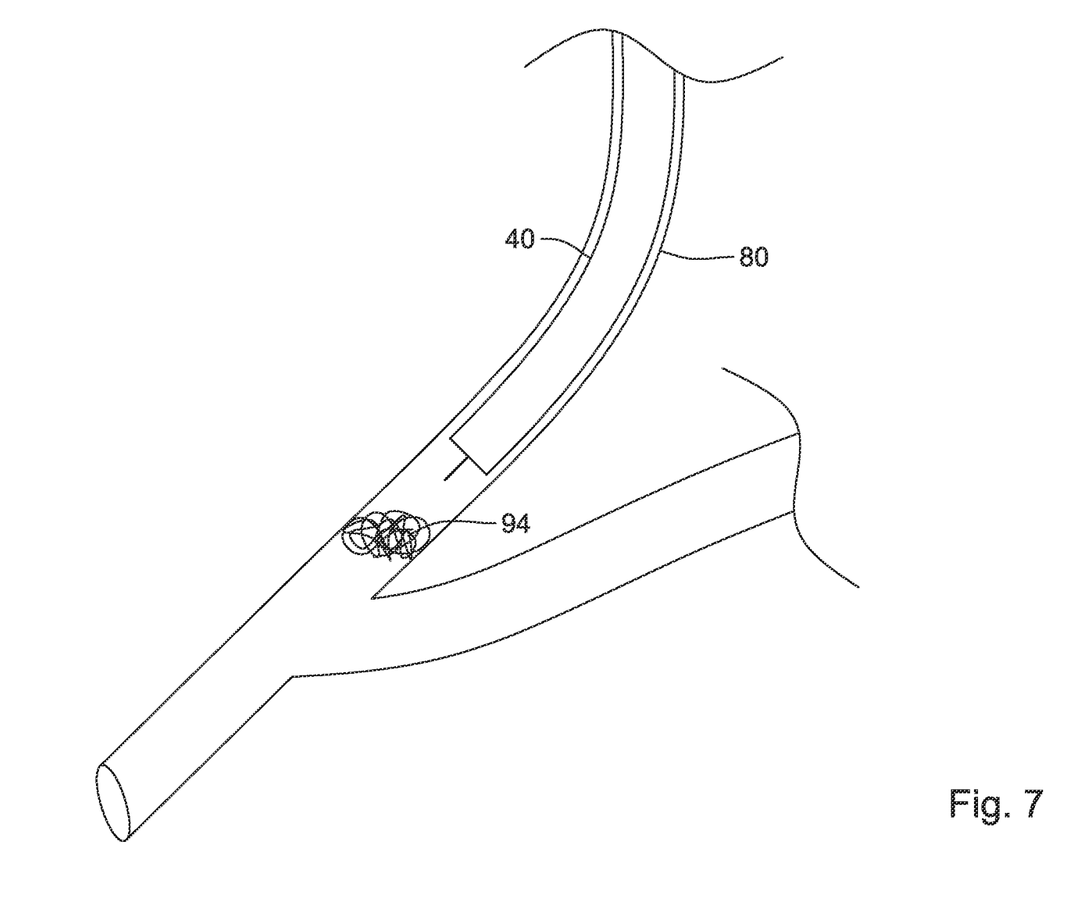
Figure 8:
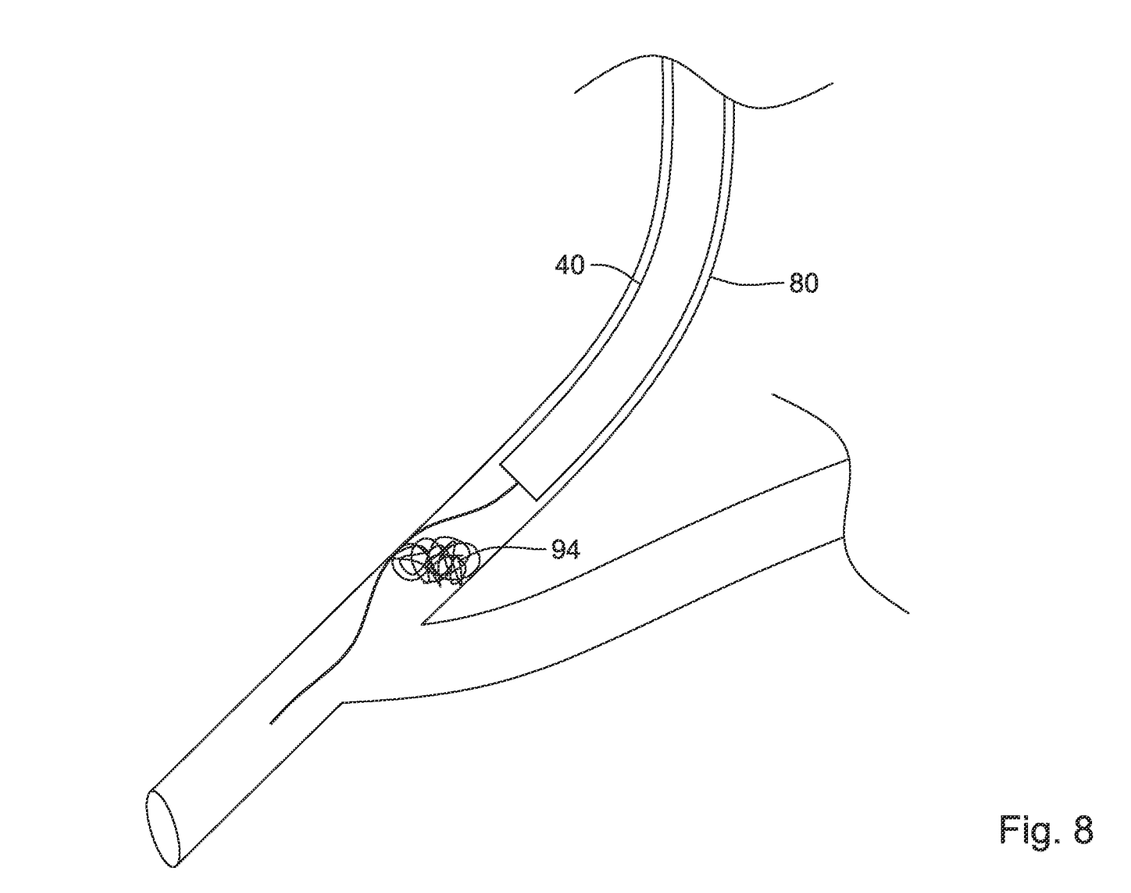

In order to cross the stricture 94, the guidewire 10 may be navigated toward the stricture 94 (e.g., through the introducer sheath 40, a guide catheter, and/or the like) as schematically depicted in FIG. 7. When navigating the guidewire 10 through tissue, it may be desirable to vary (e.g., increase) the stiffness. In some of these and in other instances, the stiffness may be further varied (e.g., the stiffness may be decreased) while navigating the guidewire 10 along the pancreatic and/or biliary tract toward the stricture 94. In some of these and in other instances, the stiffness may be further varied (e.g., the stiffness may be increased) while navigating the guidewire 10 beyond the stricture as depicted in FIG. 8.

The materials that can be used for the various components of the devices disclosed herein may include those commonly associated with medical devices. For simplicity purposes, the following discussion makes reference to the guidewire 10. However, this is not intended to limit the devices and methods described herein, as the discussion may be applied to other similar tubular members and/or components of tubular members or devices disclosed herein.

The guidewire 10 may be made from or otherwise includes a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A guidewire for use along the biliary and/or pancreatic tract, the guidewire comprising:
   an elongate core member having a proximal end region and a distal end region;
   a coil member disposed along the distal end region;
   an actuation member coupled to the coil member and disposed between the core member and the coil member, the actuation member extending along an exterior of the core member proximal of the coil member, the actuation member being configured to shift the coil member between a first configuration and a compressed configuration;
   wherein the actuation member is configured to be proximally retracted to apply compressive forces onto the coil member;
   wherein the coil member is configured to be advanced across a biliary and/or pancreatic stricture when in the compressed configuration; and
   a sleeve disposed over the coil member.

2. The guidewire of claim 1, wherein the actuation member includes a wire.

3. The guidewire of claim 1, wherein the actuation member includes a stranded cable.

4. The guidewire of claim 1, wherein the actuation member is secured to a distal end of the coil member.

5. The guidewire of claim 1, further comprising a handle coupled to the actuation member.

6. The guidewire of claim 1, further comprising a tip member disposed adjacent to a distal end of the coil member.

7. The guidewire of claim 1, wherein the sleeve has a constant outer diameter.

8. A method for antegrade stricture crossing along the biliary and/or pancreatic tract, the method comprising:
   advancing a variable stiffness guidewire to a position adjacent to a stricture along the biliary and/or pancreatic tract;
   wherein the variable stiffness guidewire comprises:
   an elongate core member having a proximal end region and a distal end region,
   a coil member disposed along the distal end region,
   an actuation member coupled to the coil member and disposed between the core member and the coil member, the actuation member extending along an exterior of the core member proximal of the coil member, the actuation member being configured to shift the coil member between a first configuration and a compressed configuration, and
   a sleeve disposed over the coil member;
   actuating the actuation member longitudinally towards the proximal end region, to shift the coil member to the compressed configuration; and
   advancing the variable stiffness guidewire across the stricture.

9. The method of claim 8, wherein advancing a variable stiffness guidewire to a position adjacent to a stricture along the biliary and/or pancreatic tract includes advancing the variable stiffness guidewire through an endoscope.

10. The method of claim 8, wherein advancing a variable stiffness guidewire to a position adjacent to a stricture along the biliary and/or pancreatic tract includes advancing the variable stiffness guidewire through a wall of the duodenum.

11. The method of claim 8, wherein the actuation member includes a wire.

12. The method of claim 8, wherein the actuation member includes a stranded cable.

13. The method of claim 8, wherein the actuation member is secured to a distal end of the coil member.

14. The method of claim 8, further comprising a handle coupled to the actuation member, and wherein actuating the actuation member includes actuating the handle.

15. The method of claim 8, further comprising a tip member disposed adjacent to a distal end of the coil member.

16. The method of claim 8, wherein the sleeve has a constant outer diameter.

17. A variable stiffness guidewire, the variable stiffness guidewire comprising:
   an elongate shaft having a proximal end region and a distal end region;
   a coil member surrounding and coupled to the distal end region, the coil member having a proximal end and a distal end;

an actuation member coupled to the coil member, the actuation member extending toward the proximal end region of the elongate shaft along an exterior of the elongate shaft proximal of the proximal end of the coil member, the actuation member being configured to shift the coil member between a first configuration and a compressed configuration;

wherein the elongate shaft and the actuation member are separate structures;

wherein the actuation member is configured to move in a longitudinal direction relative to the elongate shaft to apply compressive forces onto the coil member;

wherein the coil member is configured to be advanced across a biliary and/or pancreatic stricture when in the compressed configuration; and a sleeve disposed over the coil member.

18. The variable stiffness guidewire of claim 17, further comprising a handle coupled to the actuation member and to the proximal end region of the elongate shaft.

19. The variable stiffness guidewire of claim 17, further comprising a tip member disposed adjacent to the distal end of the coil member.

20. The variable stiffness guidewire of claim 17, wherein the sleeve has a constant outer diameter.

* * * * *